(12) United States Patent
Castro et al.

(10) Patent No.: US 6,508,966 B1
(45) Date of Patent: Jan. 21, 2003

(54) SPLITTABLE TUBULAR MEDICAL DEVICE AND METHOD FOR MANUFACTURE

(75) Inventors: Cynthia Anne Castro, Sandy, UT (US); Lesle Ann Wilkinson, Sandy, UT (US); Steven Wayne Johnson, West Jordan, UT (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/272,157

(22) Filed: Mar. 19, 1999

Related U.S. Application Data

(62) Division of application No. 08/996,023, filed on Dec. 22, 1997.

(51) Int. Cl.[7] .............................................. B29C 37/02
(52) U.S. Cl. ....................... 264/138; 264/296; 264/322; 264/519; 264/327; 425/403; 425/393; 604/523
(58) Field of Search ............................. 604/523, 164.04, 604/164.01, 264, 164; 264/171.26, 167, 165, 2.2, 2.5, 177.1, 173.17, 635, 638, 645, 560, 519, 327, 320, 322, 138, 145, 296; 425/403, 393; 156/244.11, 244.13, 244.18, 244.19, 294

(56) References Cited

U.S. PATENT DOCUMENTS

| | | | | |
|---|---|---|---|---|
| 3,843,300 A | * | 10/1974 | McFarlane | 219/385 |
| 3,944,641 A | * | 3/1976 | Lemelson | 264/145 |
| 4,345,606 A | * | 8/1982 | Littleford | 604/164.05 |
| 4,404,159 A | * | 9/1983 | McFarlane | 264/296 |
| 4,661,300 A | * | 4/1987 | Daugherty | 264/163 |
| 4,753,765 A | * | 6/1988 | Pande | 264/149 |
| 4,997,424 A | * | 3/1991 | Little | 30/90.4 |
| 5,032,343 A | * | 7/1991 | Jeffs et al. | 264/320 |
| 5,104,388 A | * | 4/1992 | Quackenbush | 604/164.05 |
| 5,320,602 A | * | 6/1994 | Karpiel | 600/101 |
| 5,397,311 A | * | 3/1995 | Walker et al. | 604/160 |
| 5,843,356 A | * | 12/1998 | Patel et al. | 264/161 |
| 5,961,765 A | * | 10/1999 | Kastenhofer | 156/242 |
| 5,985,195 A | * | 11/1999 | Muskatello | 264/161 |
| 6,083,440 A | * | 7/2000 | Matsumoto et al. | 264/138 |
| 6,251,119 B1 | * | 6/2001 | Addis | 128/898 |
| 6,358,460 B1 | * | 3/2002 | Hunt et al. | 264/113 |

FOREIGN PATENT DOCUMENTS

| | | | | |
|---|---|---|---|---|
| JP | 04093207 A | * | 3/1992 | B29C/33/42 |

* cited by examiner

Primary Examiner—Henry Bennett
Assistant Examiner—Kathryn Ferko
(74) Attorney, Agent, or Firm—James J. Murtha

(57) ABSTRACT

This invention relates to a splittable medical device incorporating two sets of preferential tear lines. The first set of preferential tear lines preferably includes two longitudinally extending skives formed along the exterior surface of the proximal portion of the splittable medical device. The second set of preferential tear lines preferably includes a plurality of grooves formed along a distal portion of the interior portion of the splittable medical device. The skives should be substantially aligned with some of the grooves. This configuration facilitates splitting of the medical device along the skives and along one or more of the grooves to allow a clinician to split the medical device completely into two pieces. This invention includes a special mandrel having a plurality of ribs formed along a distal portion thereof and process that is used to manufacture the splittable medical device.

5 Claims, 11 Drawing Sheets

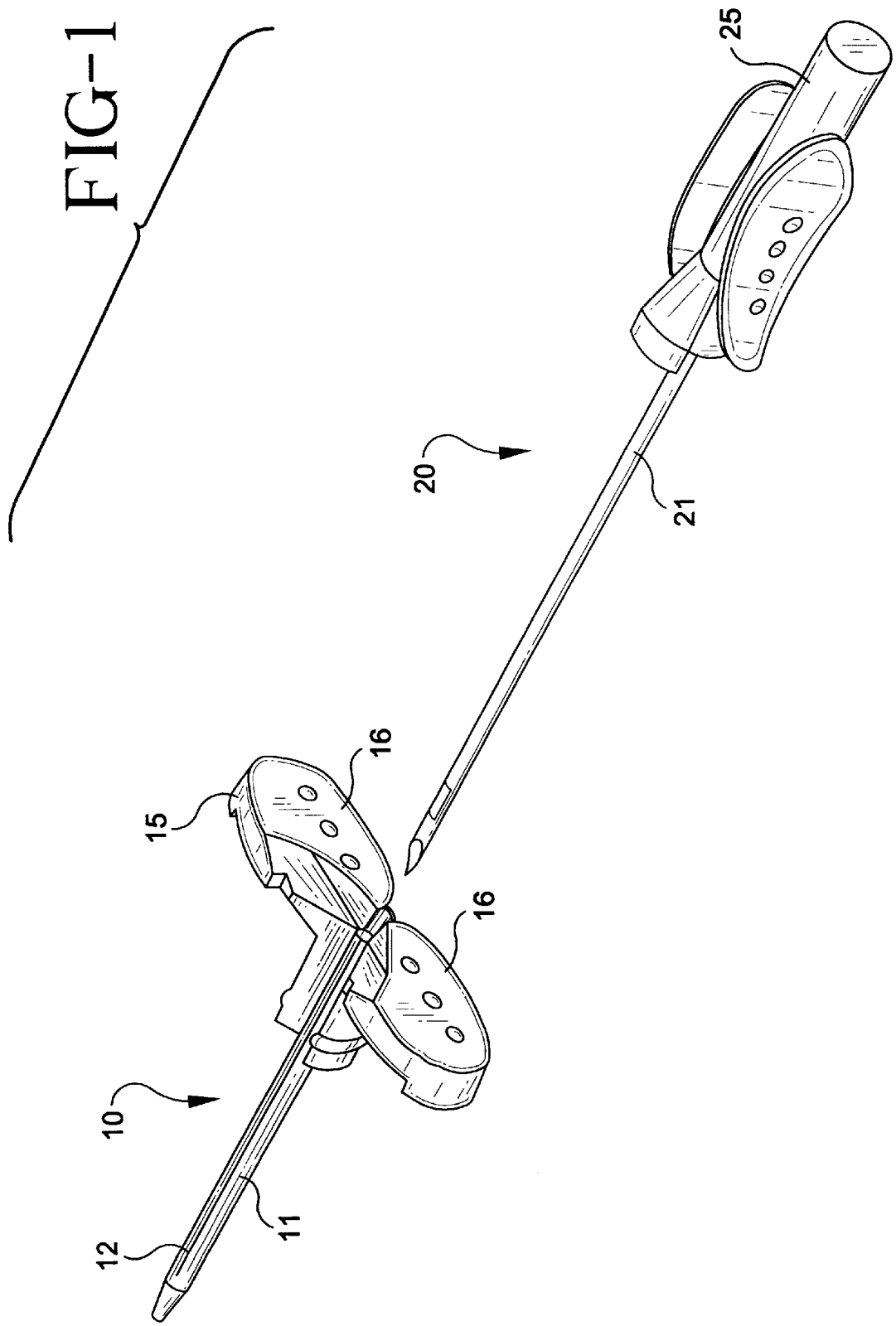

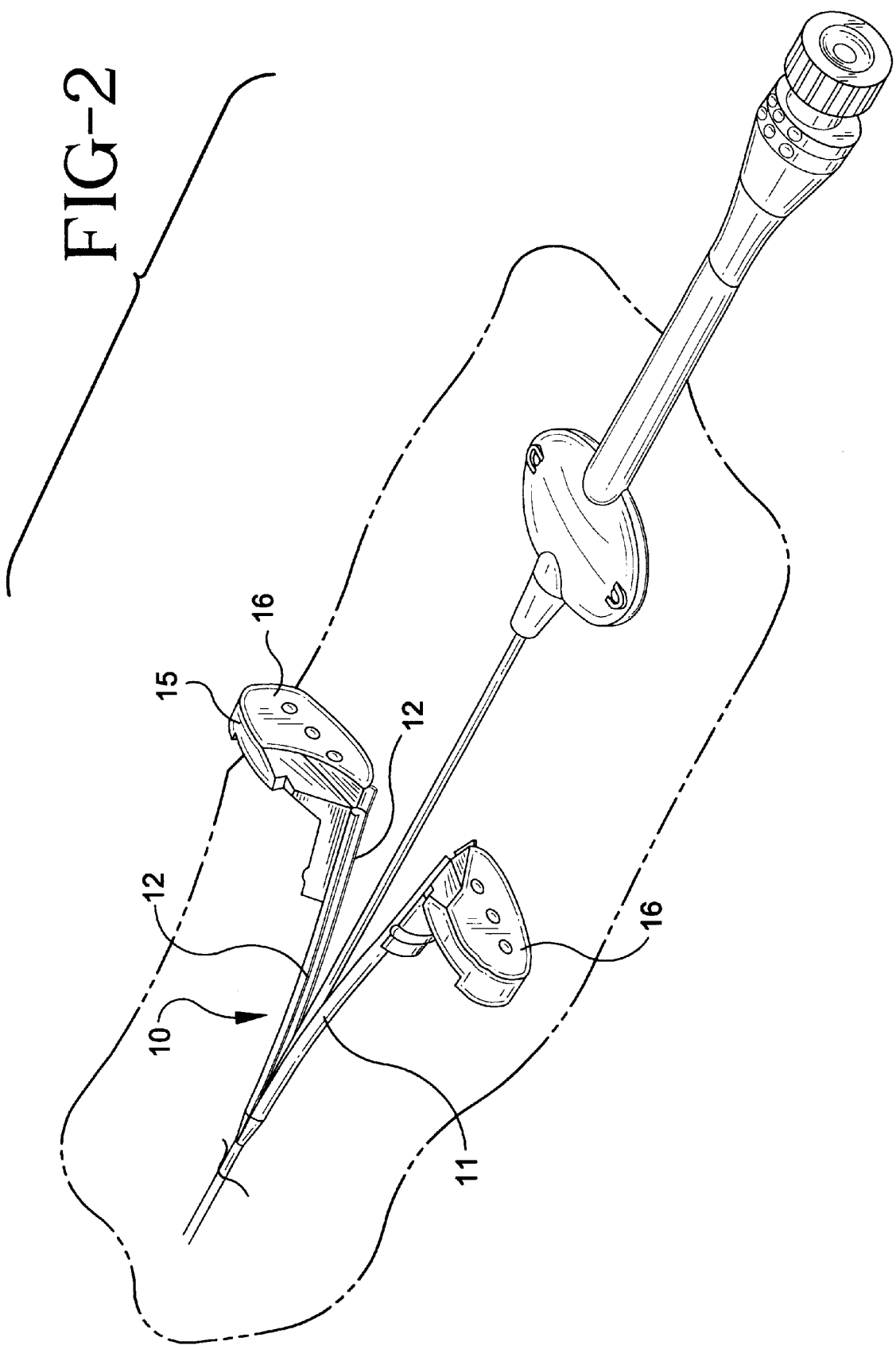

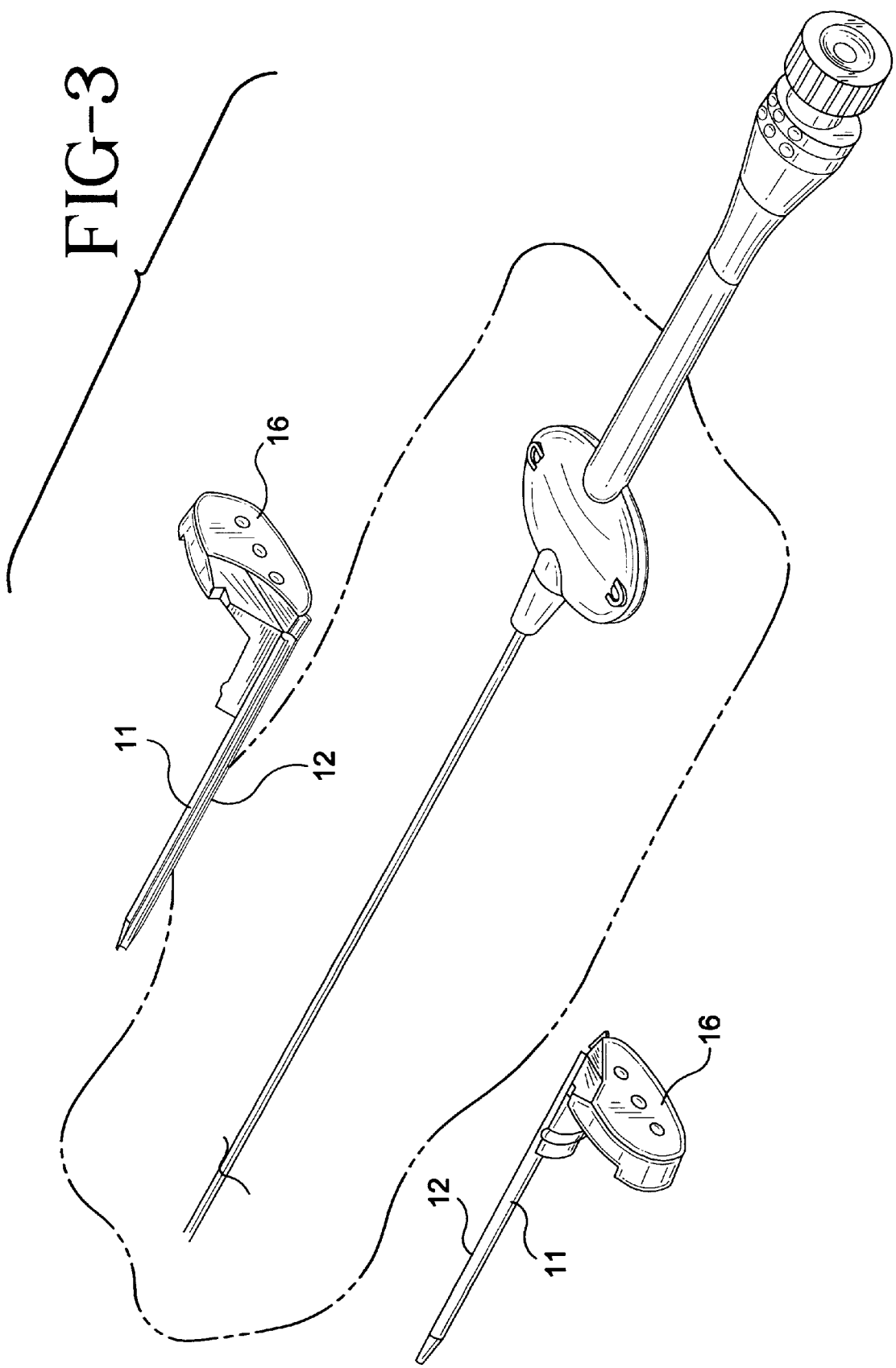

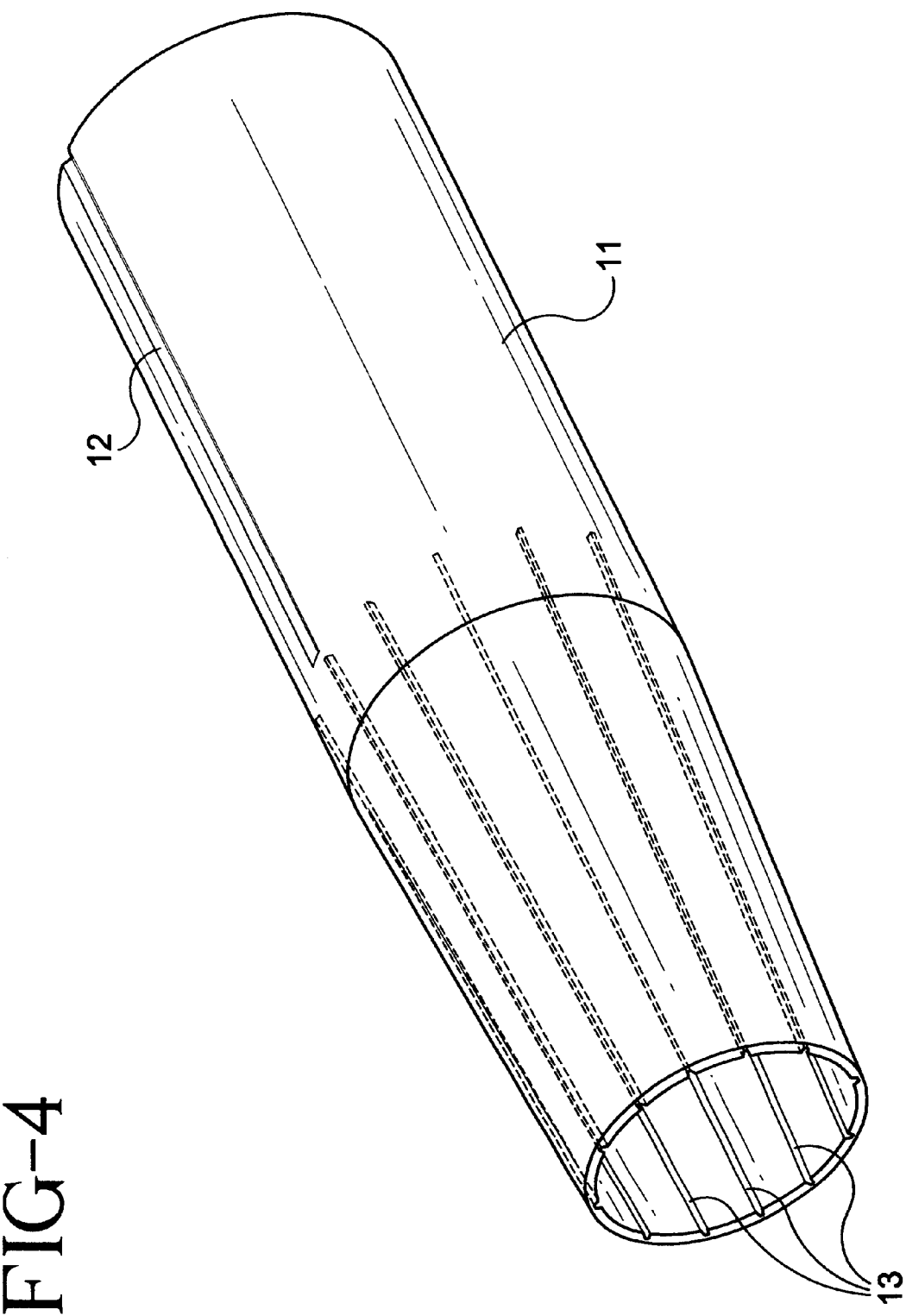

SPLITTABLE TUBULAR MEDICAL DEVICE AND METHOD FOR MANUFACTURE

This is a division of application Ser. No. 08/996,023 filed Dec. 22, 1997.

BACKGROUND OF THE INVENTION

This invention relates generally to the field of medical devices and more particularly to the field of medical devices for use in infusion therapy and even more particularly to catheters and catheter introducers.

Catheters, particularly intravenous (IV) catheters, are used for directing fluid into or withdrawing fluid from a patient. The most common type of IV catheter is an over the needle peripheral IV catheter. As its name implies, an over the needle catheter is mounted over an introducer needle having a sharp distal tip. The catheter and the introducer needle are assembled so that the distal tip of the introducer needle extends beyond the distal tip of the catheter. The resulting assembly is inserted through the patient's skin into a peripheral blood vessel, i.e. a smaller blood vessel that is not connected directly to the heart but is one of the branches of the central blood vessels that are directly connected to the heart. Once placement of the assembly in the blood vessel is verified by flashback of blood in the needle and in a flashback chamber located at the proximal end of the needle, the needle is withdrawn leaving the catheter in place. Peripheral IV catheters tend to be relatively short, and are on the order of about one and one-half inches in length. Such catheters are used to infuse fluid such as normal saline solution, various medicaments and total parenteral nutrition to treat the patient in whom the catheter is placed.

Another type of IV catheter is a peripherally inserted central catheter (PICC). This catheter is substantially longer than a standard peripheral IV catheter. It is placed in a peripheral blood vessel but is advanced through the vasculature so that typically the distal tip of the catheter is in one of the central blood vessels such as the superior vena cava and is adjacent to the heart. PICCs are typically used for extended infusion therapy protocols. In order to place a PICC into a patient, a catheter introducer is used because a typical PICC does not have sufficient column strength to be inserted into a blood vessel in the same way that a standard peripheral IV catheter is placed in a blood vessel.

A catheter introducer is a polymeric tubular member having a hub at its proximal end to facilitate manipulation of the device. The catheter introducer is used with an introducer needle in much the same manner that a standard over the needle peripheral IV catheter is used with an introducer needle. Thus the catheter introducer is located coaxially over the introducer needle with the distal end of the introducer needle extending distally beyond the distal end of the catheter introducer. The catheter introducer and introducer needle assembly is placed into a peripheral blood vessel in much the same manner that a standard over the needle peripheral IV catheter is placed into a patient's blood vessel. When the catheter introducer and introducer needle assembly is properly located in the appropriate blood vessel, the introducer needle is removed from the catheter introducer. A PICC is then inserted through the catheter introducer and advanced through the vasculature into its proper location. Alternatively, a guidewire may be inserted through the catheter introducer first so that when the PICC is inserted over the guidewire and through the catheter introducer, the guidewire acts as a track for the PICC to facilitate proper placement of the PICC. Once the PICC is properly placed in the vasculature, the catheter introducer is removed from the patient leaving only the PICC behind.

In order to remove the catheter introducer from the patient with a PICC inserted therethrough, the catheter introducer must be split into two pieces in order for it to be removed from the patient. The catheter introducer cannot be simply withdrawn proximally over the PICC because the PICC typically has a proximal hub or other configuration adjacent to its proximal end that is larger than the internal diameter of the catheter introducer. Thus when the distal end of the PICC is inserted into the patient through the catheter introducer, the proximal hub on the catheter introducer blocks the proximal withdrawal of the catheter introducer from the PICC. The solution to this problem is to have the body of the catheter introducer formed with two longitudinal extending preferential tear lines that are generally about 180 degrees apart or at least substantially displaced from one another to allow the catheter introducer to be split into two pieces. Such tear lines facilitate splitting of the catheter introducer. These preferential tear lines are generally formed by skiving, i.e. cutting the preferential tear lines into the exterior of the tubular body of the catheter introducer by a knife or some sharp blade. Such a process typically works for its intended purpose but manufacturing problems do exist.

The distal portion of the catheter introducer is preferably formed with a taper having a particular configuration. Such a taper is typically used for standard peripheral over the needle IV catheters and is disclosed in U.S. Pat. No. 4,588,398. This configuration facilitates insertion of the catheter or the catheter introducer into the patient and minimizes peel back or other deformation along the distal portion of the catheter or catheter introducer that could result in patient discomfort. Various processes can be used to form such a tapered distal portion. However, a particularly preferred process is disclosed in U.S. Pat. No. 4,661,300. This process involves the following steps: placing a blank, i.e. a tube that will be used as the catheter or catheter introducer, onto a mandrel, heating at least the distal tip of the blank, engaging the mandrel with a die having the shape desired for the distal portion of the catheter or catheter introducer, removing the die from engagement with the mandrel and removing the tipped blank from the mandrel.

Although this process forms the desired tapered distal portion on the catheter introducer, the process melts, and thus eliminates, the skive on the blank at least along the distal portion of the catheter introducer. This results in a catheter introducer having no preferential tear line along its distal portion. Thus the catheter introducer cannot be easily split making it difficult for the clinician to remove the catheter introducer from the patient during the PICC insertion procedure.

SUMMARY OF THE INVENTION

It is therefore an object of the invention to provide a splittable tubular medical device.

It is another object of the invention to provide a splittable tubular medical device that has at least one longitudinally extending preferential tear line that extends along the distal portion of the device.

It is yet another object of the invention to provide a process for manufacturing a splittable medical device that allows at least one preferential tear line to be formed in and to remain in the distal portion of the medical device even where the distal portion of the medical device is heated to form a tapered distal portion.

The splittable medical device of this invention includes a main body portion in the form of a tube. The tube includes at least one and preferably a plurality of longitudinally extending preferential tear lines. One set of preferential tear lines is located along the exterior surface of the proximal portion of the tube. This set includes two such preferential tear lines located on substantially opposite sides of the tube. A second set of preferential tear lines is located along the interior surface of the distal portion of the tube. This set includes at least two such preferential tear lines with one such preferential tear line in substantial longitudinal alignment with each preferential tear line formed along the exterior surface of the proximal portion of the tube. A hub is connected to the proximal end of the tube. The first set of preferential tear lines is properly longitudinally aligned with the hub so that when the hub is pulled apart, the force applied to the hub is transmitted to the tube along the preferential tear lines to split the tube and attached hub into two separate pieces.

The splittable medical device of this invention is formed by using a special mandrel during the tipping operation. More specifically, the splittable medical device of this invention is formned by first extruding a tube having a desired diameter and wall thickness from a suitable polymer such as polyethylene, polytetrafluoroethylene or polyurethane. Next the tube is cut to the appropriate size. The tube is then connected to a suitable hub and two longitudinally extending preferential tear lines are formed along the outer surface of the tube by drawing the sharp edge of a knife against the tube. Next, the distal portion of the splittable medical device of this invention is tipped. This is done by placing the tube over a specially designed mandrel, heating the distal end of the tube to a suitable temperature so the distal portion of the tube is flowable, advancing a die into engagement with the distal portion of the mandrel to form the desired shape along the distal portion on the tube, removing the die from contact with the mandrel and removing the tipped tube from the specially designed mandrel.

The mandrel of this invention includes a plurality of longitudinally extending ribs formed along the distal portion of the mandrel. When the distal portion of the tube is tipped using this mandrel, the internal surface of the tube is altered to include a plurality of longitudinally extending grooves along the distal portion of the tube. The grooves formed on the internal surface of the tube are complementary to the ribs on the mandrel. This configuration results in longitudinally extending internal grooves being formed along the distal portion of the tube when the distal portion of the tube is tipped using the mandrel of this invention. These grooves are preferential tear lines that are substantially longitudinally aligned with the skives, i.e. preferential tear lines, formed along the portion of the tube proximal to the internal grooved portion of the tube. Thus even though the heat used to tip the tube may melt and eliminate the skive earlier formed on the outer surface of the tube, substantially the entire length of the tube is formed with preferential tear lines which facilitate splitting of the entire length of the tube.

The above and other objects and advantages of the invention will be apparent upon consideration of the following detailed description.

BRIEF DESCRIPTION OF THE DRAWINGS

The preferred embodiments are illustrated in the drawings in which like reference numerals refer to like elements and in which:

FIG. 1 is a perspective view of the catheter introducer of this invention and an associated introducer needle used therewith;

FIG. 2 is a perspective view of the catheter introducer of this invention after a PICC has be inserted therethrough and the catheter introducer has been partially split along the first set of preferential tear lines;

FIG. 3 is a perspective view of the catheter introducer of this invention after a PICC has been inserted therethrough and the catheter introducer has been completely split along the first and second set of preferential tear lines;

FIG. 4 is a perspective view of the distal portion of the catheter introducer of this invention;

DETAILED DESCRIPTION OF THE INVENTION

Figure 5A:
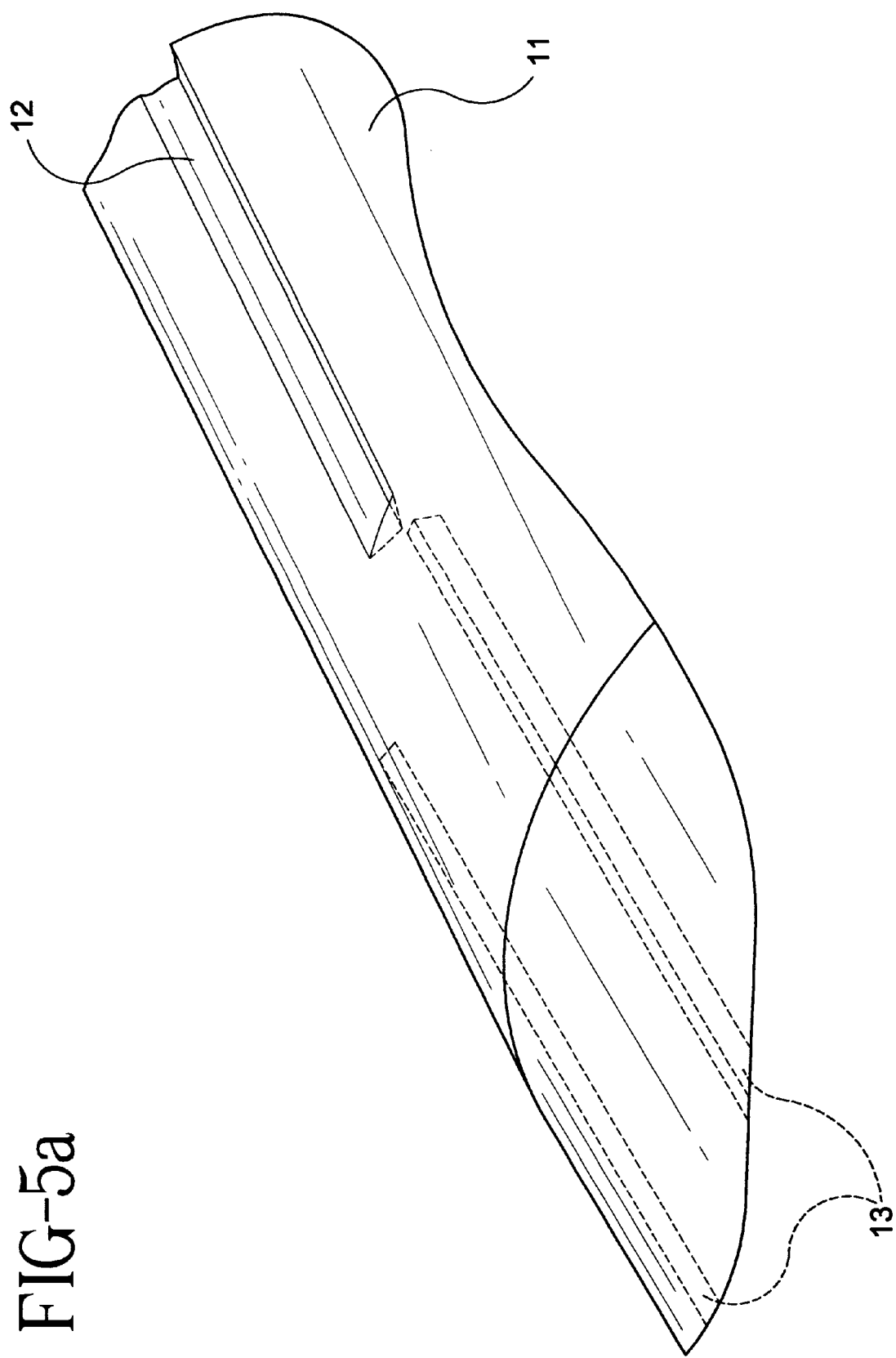
FIG. 5a is an enlarged detailed perspective view of the distal portion of one embodiment of the catheter introducer of this invention.

As used herein, the term "proximal" refers to a location on the splittable medical device of this invention closest to the clinician using the device and farthest from the patient in connection with whom the device is used. Conversely, the term "distal" refers to a location on the splittable medical device of this invention farthest from the clinician using the device and closest to the patient in connection with whom the device is used.

Although the splittable medical device of this invention is described herein as being a splittable catheter introducer that is particularly adapted for use in facilitating the insertion of a PICC into a patient, it is to be understood that this invention has applicability to catheters in general and to other medical devices that are splittable or that require a particular geometry formed on an internal surface thereof.

The catheter introducer 10 of this invention includes a main body portion in the shape of a tube 11 and a hub 15 connected to tube 11 at its proximal end. Hub 15 includes a pair of wings 16 on substantially opposite sides of hub 15. Wings 16 facilitate splitting of catheter introducer 10 as described in more detail below. Catheter introducer 10 is used in conjunction with an introducer needle 20 which includes a cannula 21 and a hub 25 located at its proximal end. Hub 25 can include a flashback chamber and a porous plug (not shown) located within the open proximal end of the flashback chamber to allow blood to flash back into the flashback chamber when the distal end of cannula 21 is properly inserted into a vein. Catheter introducer 10 is located about introducer needle 20 such that tube 11 is coaxially disposed about cannula 21. In this arrangement the sharp distal end of cannula 21 is located distal of the distal end of tube 11. This configuration facilitates the introduction of the distal end of tube 11 and cannula 21 into a patient's vein since the leading edge of the combination is the sharp distal tip of cannula 21.

To ease the insertion of tube 11 into a patient's vein, it is important that the distal end of tube 11 has a particular tapered configuration so that tube 11 can easily follow the sharp distal tip of cannula 21 past the patient's skin and subcutaneous tissue and into the patient's vein. U.S. Pat. No. 4,588,398 discloses a preferred tapered configuration for the distal portion of tube 11. The disclosure of U.S. Pat. 4,588,398 is hereby specifically incorporated into this specification by reference.

Tube 11 also includes a first set of preferential tear lines. This set includes at least one, and preferably two, longitudinally extending preferential tear lines 12 extending along the proximal portion of tube 11. These preferential tear lines 12 are weakened portions of tube 11 that allow tube 11 to be split along these lines. Preferential tear lines 12 are typically cut marks formed in the material of tube 11 by moving the sharp cutting edge of a knife or other blade along the material of tube 11. Thus, preferential tear lines 12 are typically formed along the outer surface of tube 11. Preferential tear lines 12 allow a clinician to grasp wings 16 and pull wings away from the axis of hub 15 to tear tube 11 into two separate pieces. Preferably, preferential tear lines 12 are formed substantially on opposite sides of tube 11 so they are about 180 degrees apart. In this way, tube 11 can be split in half. Although this orientation for preferential tear lines 12 is preferred, preferential tear lines could be located closer together as long as they are oriented on tube 11 so that tube 11 can be separated into two separate pieces.

During the manufacture of tube 11, preferential tear lines 12 extend along the entire length of tube 11 from its proximal end to its distal end. Unfortunately, in subsequent stages of the manufacture of catheter introducer 10, preferential tear lines 12 are eliminated from the distal portion of tubular member 11. This typically occurs when the distal portion of tube 11 is "tipped", i.e. when the distal portion of tube 11 is heated to facilitate the formation of a particular tapered configuration along the distal portion of tube 11. When the distal portion of tube 11 is heated to form the tapered configuration, the material of tube 11 becomes flowable so that any skive marks formed in the material essentially close. This eliminates preferential tear lines 12 at least along the distal portion of tube 11. Without such preferential tear lines 12 extending along the distal portion of tube 11, a clinician attempting to split tube 11 will have difficulty completely splitting tube 11 into two separate pieces.

In order to avoid this problem, a second set of preferential tear lines is formed along the distal portion of tube 11. This second set of preferential tear lines includes a plurality of grooves 13 that are formed along the distal portion of the interior of tube 11. These grooves 13 extend along that portion of tube 11 that was heated and tipped. One groove 13 should be substantially longitudinally aligned with each preferential tear line 12. In addition, grooves 13 should extend from the distal end of preferential tear lines 12 in substantially abutting relationship and extend to adjacent the distal end of tube 11. Preferably grooves 13 overlap with preferential tear lines 12. In this manner, tube 11 will have preferential tear lines longitudinally extending along substantially the entire length of tube 11 from its proximal end to its distal end. This will facilitate the splitting of tube 11 into two separate pieces. However, it is important that the distal end of grooves 13 do not extend to the very distal tip of tube 11 in order to prevent any deleterious effect on the structural integrity of the distal portion of tube 11. For a polyethylene tube with a nominal wall thickness of 0.007 inches, the distal portion of tube 11 that is distal of grooves 13 should be between about 0.007 inches and about 0.015 inches long. If this distance were any shorter, then a smooth, cleanly formed tipped could not be formed. If this distance were any longer, then any tear propagated along grooves 13 may not extend to the very distal tip of tube 11 making it difficult to easily split tube 11 into two separate pieces.

Figure 5B:
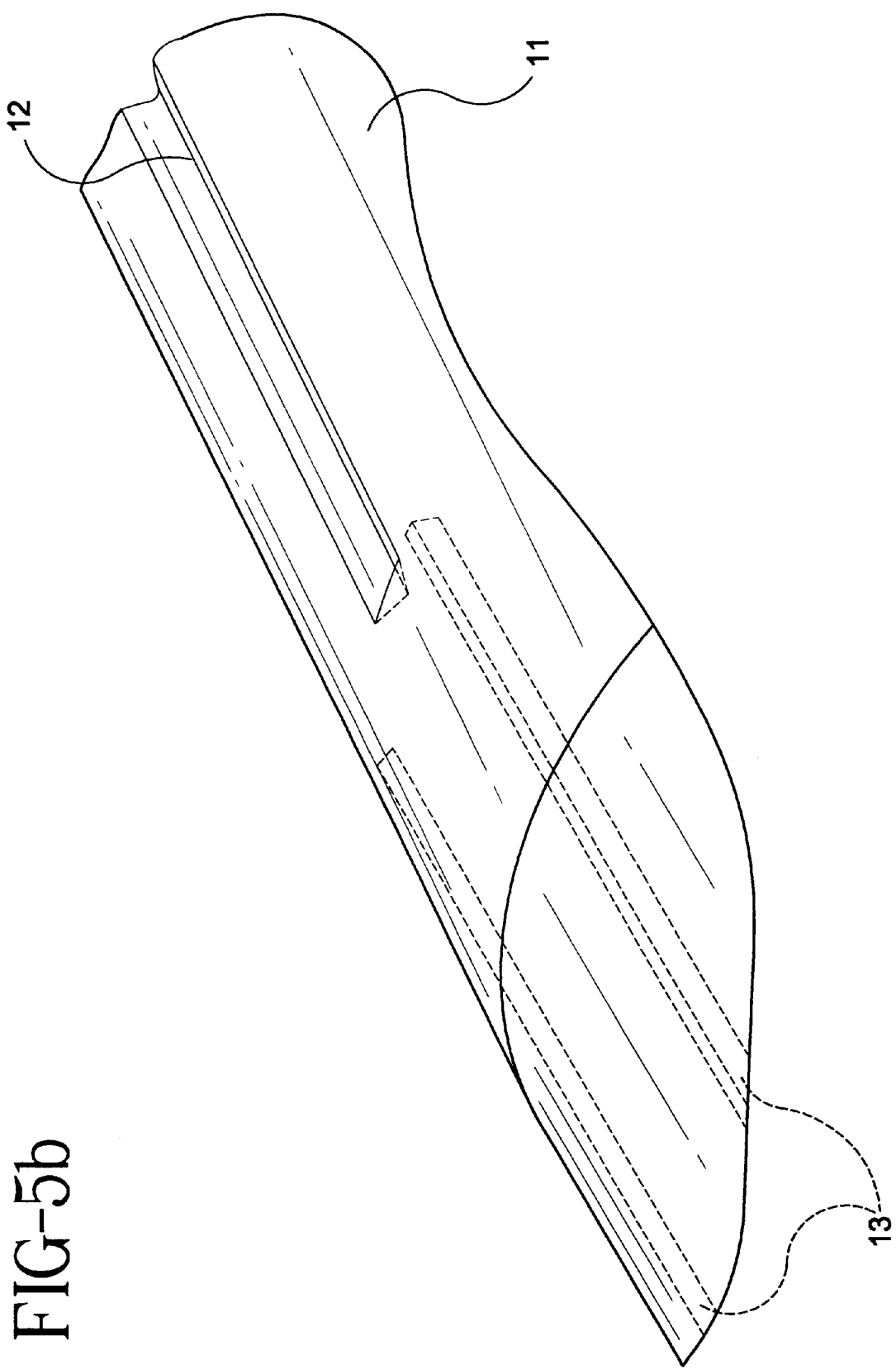
FIG. 5b is an enlarged detailed perspective view of the distal portion of another embodiment of the catheter introducer of this invention.
Figure 6:
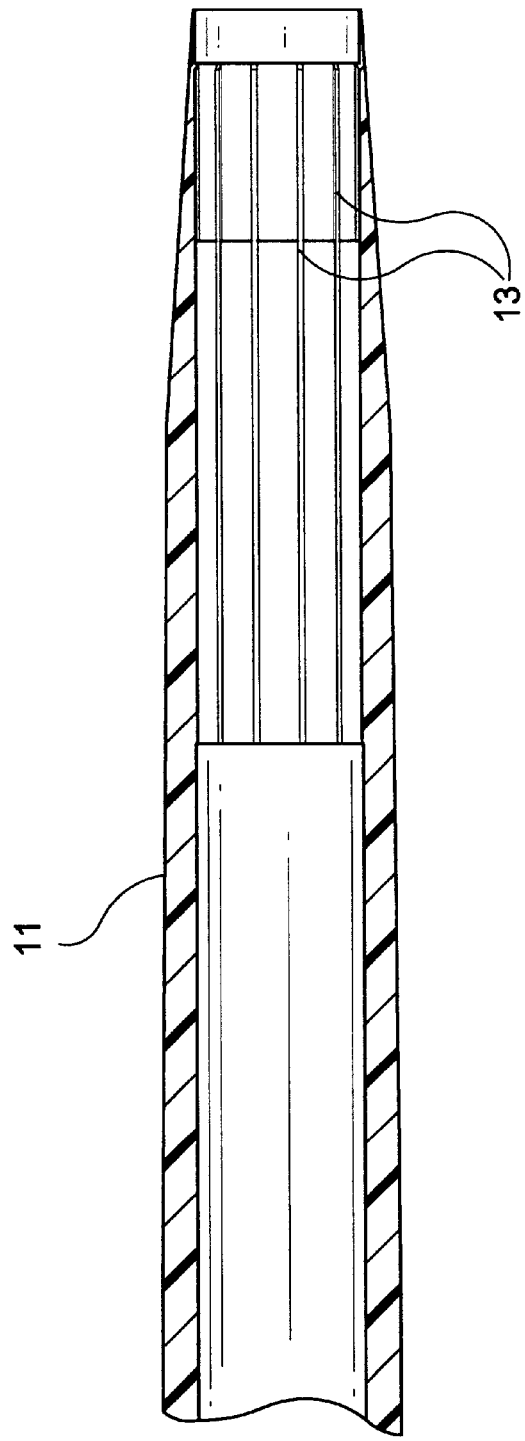
FIG. 6 is a side elevation view in cross section of the distal portion of the catheter introducer of this invention.

Although it is preferred that a groove 13 should be substantially longitudinally aligned with each preferential tear line 12, see FIG. 5a, this orientation is not critical. As long as a proximal end of a groove 13 is adjacent to a distal end of a preferential tear line 12, any tear created along such a preferential tear line 12 should be able to find an adjacent groove 13 and continue tearing to the distal end of tube 11. See for example FIG. 5b. For a 2 French tube, it has been found that the grooves 13 should be about 45 degrees apart. For a 3 French tube, it has been found that the grooves 13 should be about 30 degrees apart.

Figure 7:
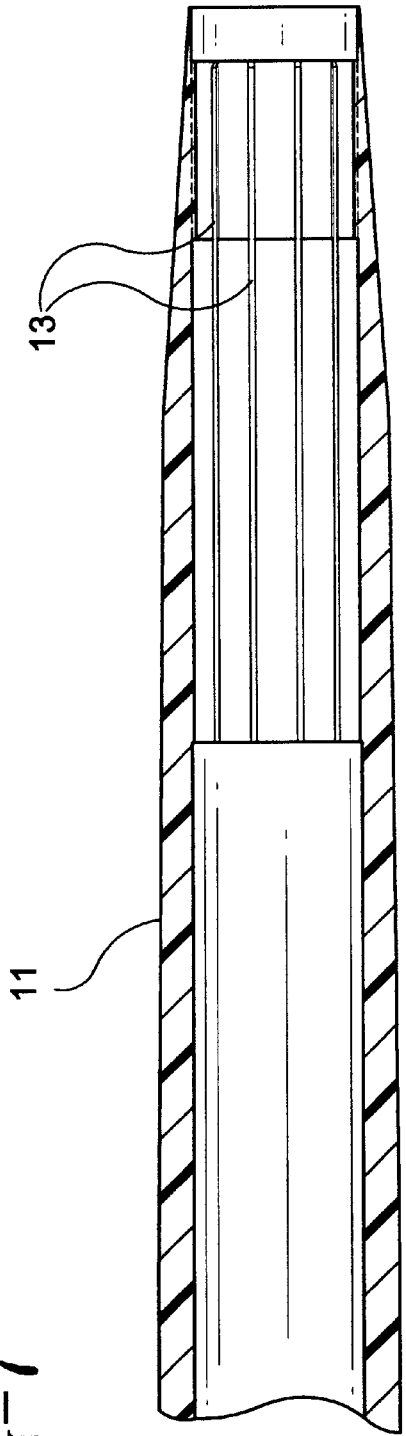
FIG. 7 is a side elevation view in cross section of another embodiment of the distal portion of the catheter introducer of this invention.
Figure 8:
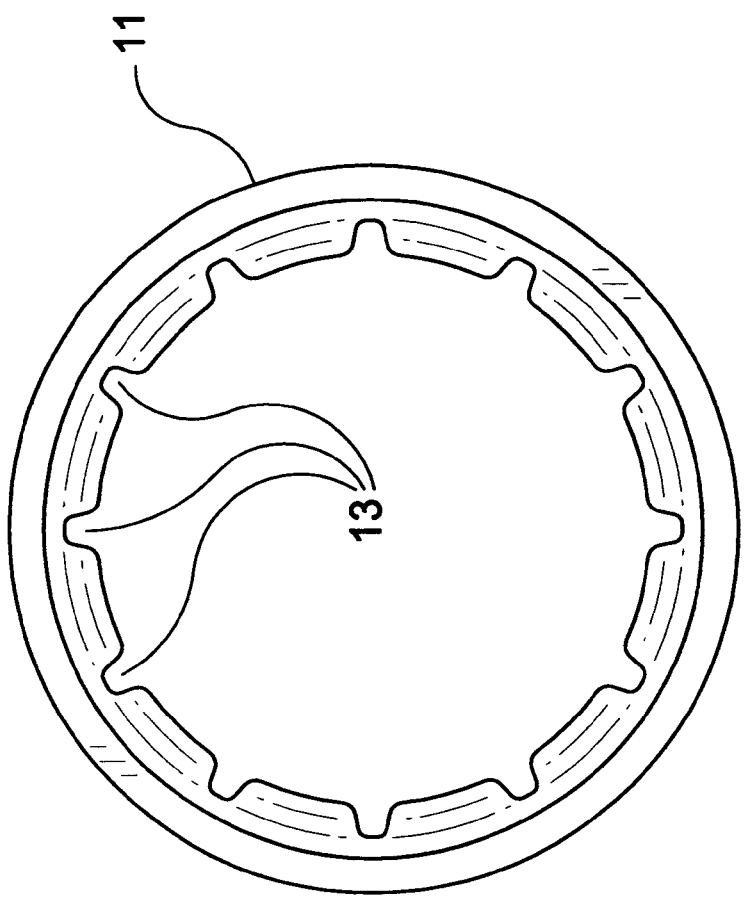
FIG. 8 is an end elevation view in cross section of the catheter introducer of this invention.
Figure 9:
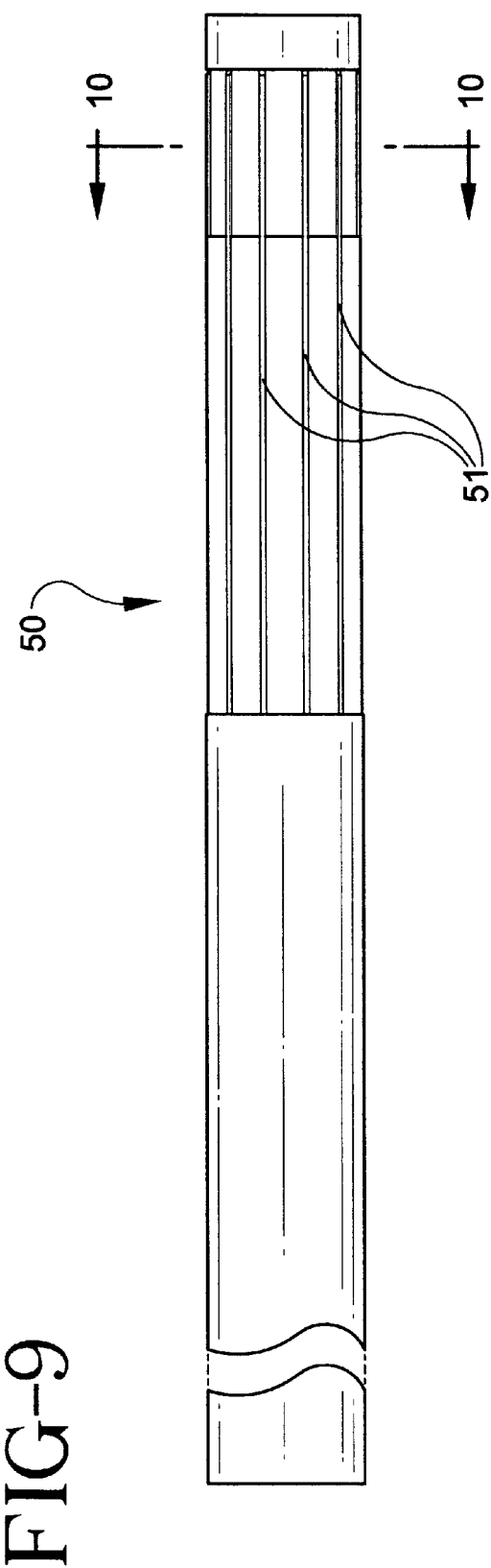
FIG. 9 is side elevation view of the mandrel of this invention that is used to form the internal grooved configuration along the distal portion of the catheter introducer of this invention.
Figure 10:
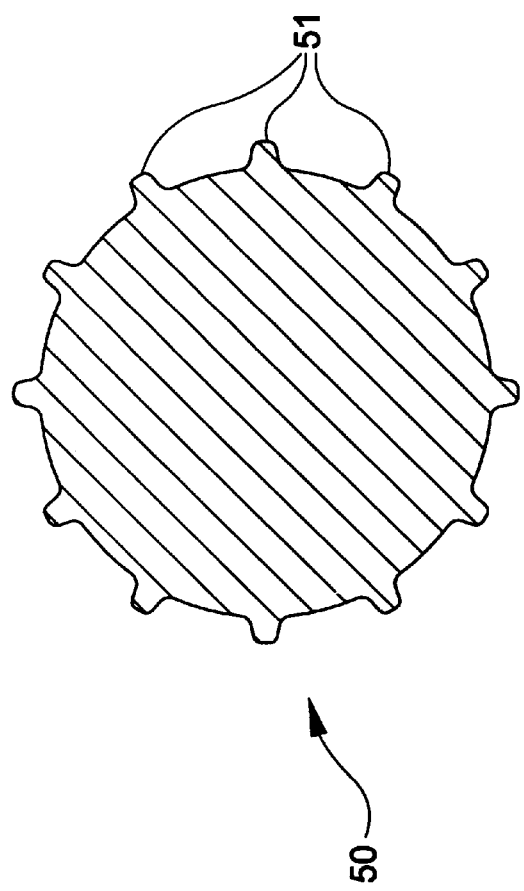
FIG. 10 is a cross sectional view, taken along line 10—10 of FIG. 9, of the mandrel of this invention that is used to form the internal grooved configuration along the distal portion of the catheter introducer of this invention.
Figure 11:
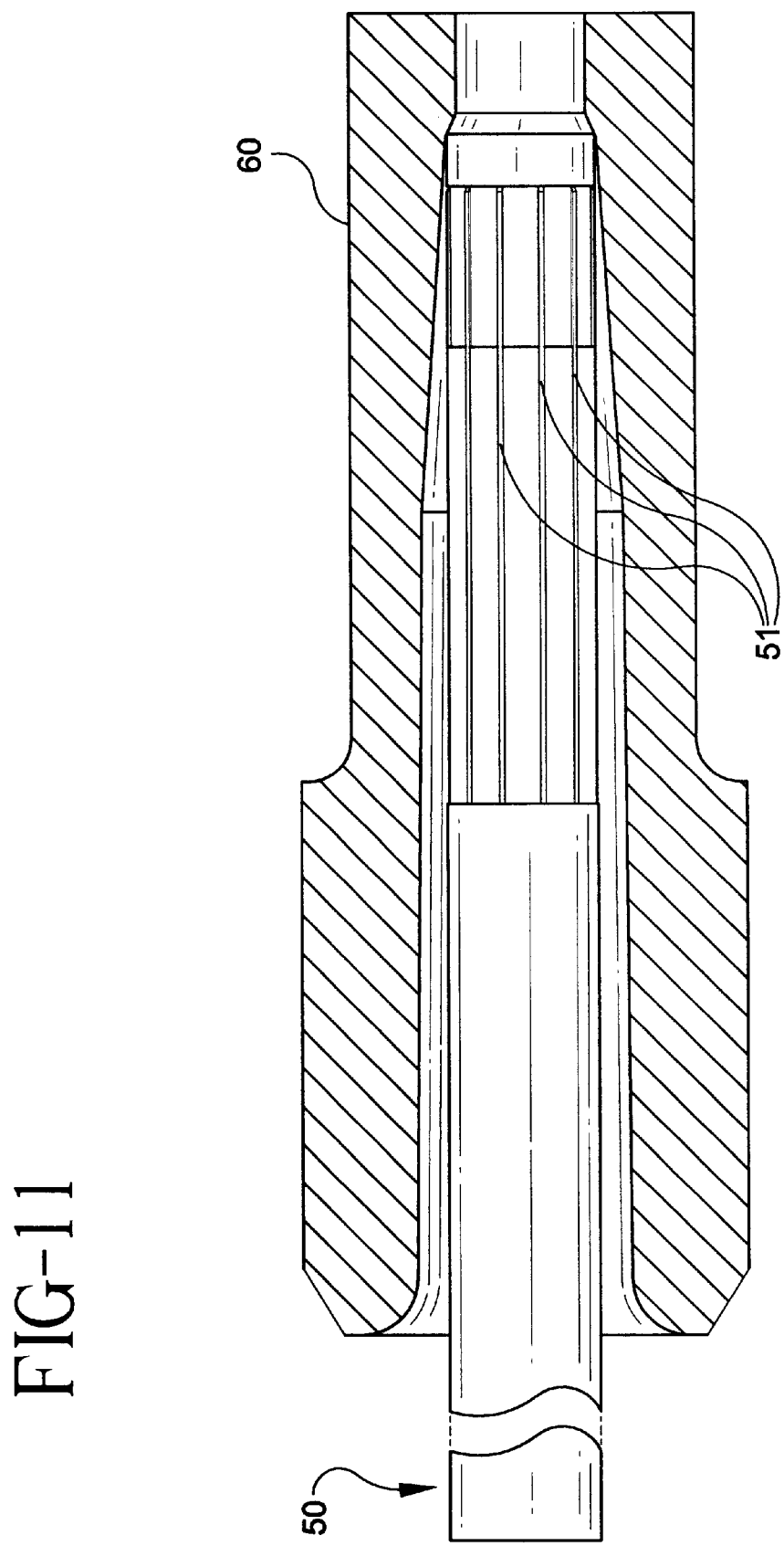
FIG. 11 is side elevation view of the mandrel of this invention that is used to form the internal grooved configuration along the distal portion of the catheter introducer of this invention and a die that is used to form the tapered distal portion of the catheter introducer of this invention.
Figure 12:
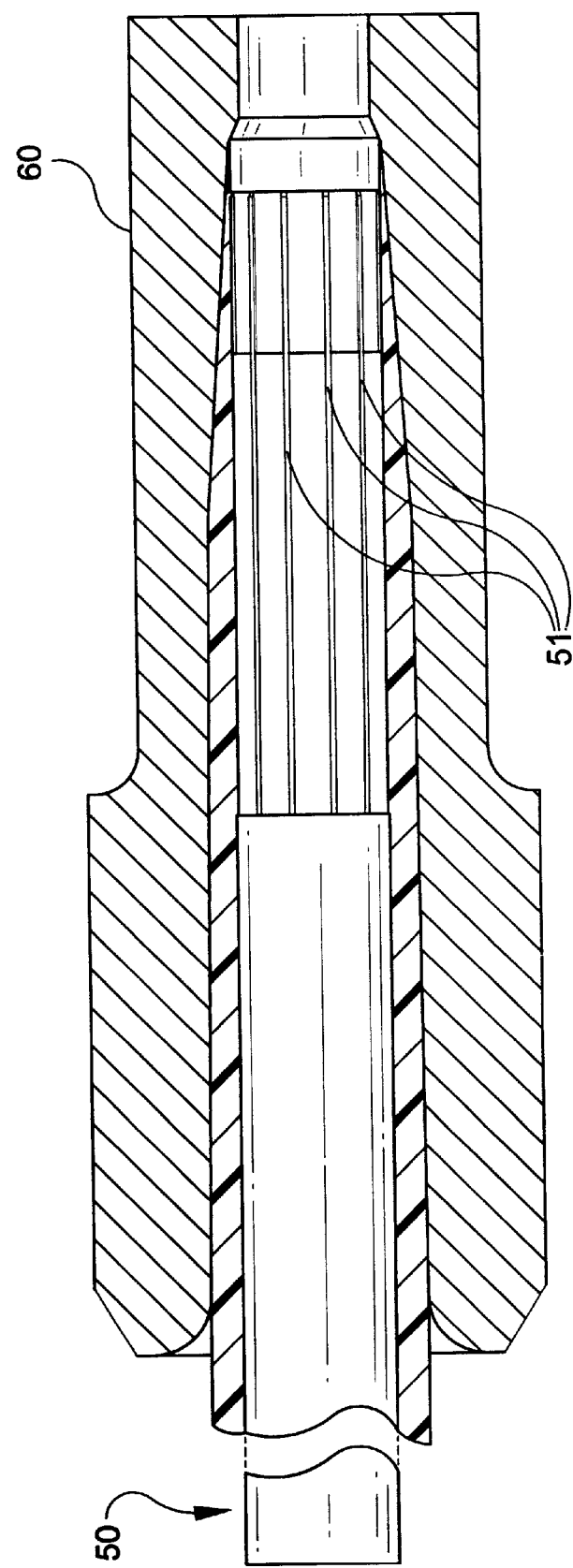
FIG. 12 is a side elevation view of the mandrel of this invention that is used to form the internal grooved configuration along the distal portion of the catheter introducer of this invention and a die that is used to form the tapered distal portion of the catheter introducer of this invention and the tapered distal portion of the catheter introducer of this invention being formed between the die and mandrel.

Although it is preferred that the distal portion of the interior of tube 11 have only that number of grooves 13 equal to the number of preferential tear lines 12 initially formed in tube 11, a larger number of grooves may be formed therein to facilitate the manufacture of catheter introducer 10. Thus in connection with the preceding discussion, it has been determined that for a 2 French tube, 8 grooves should be equiangularly spaced about the interior circumference of tube 11. For a 3 French tube, 12 grooves should be equiangularly spaced about the interior circumference of tube 11.

Where tube 11 has a nominal wall thickness of 0.007 inches, each groove 13 should be about 0.002 inches deep. Of course where tube 11 has a different wall thickness, grooves 13 may have a different depth. In addition, where the distal portion of tube 11 has a tapered configuration, grooves 13 may be formed with differing depths along their length. For example, the depth of the distal portion of grooves 13 could be less than the depth of the proximal portion of grooves 13. See FIG. 7. This ensures that the wall thickness along the distal portion of tube 11 is robust enough to avoid unduly affecting the structural integrity along the distal portion of tube 11. Thus the distal portion of grooves 13 could have a depth of about 0.0015 inches and the proximal portion of grooves 13 could have a depth of about 0.002 inches where the wall thickness is 0.007 inches.

The process of producing catheter introducer 10 will now be described. First, a tube having the desired lumen diameter and wall thickness is extruded from a suitable polymer such as polyethylene, polytetrafluoroethylene or polyurethane. Next the tube is cut to the appropriate size. The tube is then connected to a suitable hub 15 and two longitudinally extending preferential tear lines 12 are formed along the outer surface of the tube by drawing the sharp edge of a knife against the tube. These preferential tear lines are aligned with hub 15 in such a manner that wings 16 on hub 15 are substantially opposed to one another so that each wing 16 is located between each preferential tear line 12. Thus when wings 16 are pulled apart, the force applied to wings 16 is transmitted to the tube along preferential tear lines 12 to split catheter introducer 10 into two separate pieces.

Next, the distal portion of catheter introducer 10 is tipped. The tipping process is described in detail in U.S. Pat. No. 4,661,300, the disclosure of which is specifically incorporated into this specification by reference. In this process, a catheter blank, i.e. a tubular member used to form the catheter, is placed on a mandrel. A die having an interior molding surface, which is tapered according to the distal portion of the catheter desired, is aligned axially with the mandrel. The distal portion of the catheter blank is heated, typically using RF energy, so that it is flowable. The mandrel and die are brought together so the distal edge of the mandrel engages the tapered portion of the die. This action cleanly forms a smooth and uniform tapered distal portion for the catheter. In the process of this application, the distal portion of catheter introducer 10 is tipped by placing the tube over a specially designed mandrel 50. The remaining steps of a standard tipping process are used, i.e., heating the distal end of the tube to a suitable temperature so the distal portion of the tube is flowable, advancing a die 60 into engagement with the distal portion of mandrel 50 to form the desired tapered distal portion on the tube and removing die 60 from contact with mandrel 50 and removing the tipped tube from mandrel 50.

Mandrel 50 includes a plurality of longitudinally extending ribs 51 formed along the outer surface of the distal portion of mandrel 50. The number of ribs 51 formed in mandrel 50 is determined by the number of grooves 13 desired to be formed in tube 11. As discussed above, for a 3 French tube, preferably 12 grooves 13 are formed in tube 11. Thus, preferably 12 ribs 51 are formed in mandrel 50. Each rib 51 should have a height of about 0.002 inches where tube 11 has a nominal wall thickness of 0.007 inches. In addition, as discussed above, the depth of grooves 13 may not be uniform where the distal portion of tube 11 has a tapered (configuration. For example, where the distal portion of grooves 13 has a depth of about 0.0015 inches and the proximal portion of grooves has a depth of 0.002 inches, the proximal portion of each rib 51 should have a height of about 0.002 inches and the distal portion of each rib 51 should have a height of about 0.0015 inches.

When the distal portion of the tube is tipped using this mandrel, the internal surface of the tube is altered to include a plurality of longitudinally extending grooves along the distal portion of the tube. The grooves on the internal surface of the tube are complementary to the ribs on the mandrel. This configuration ensures that preferential tear lines are formed along the distal portion of the catheter introducer even though the heat used to tip the tube melts and eliminates the skive earlier formed on the outer surface of the tube.

Thus it is seen that a splittable tubular medical device is provided that has longitudinally extending preferential tear lines that extend to the distal end of the device. A process is also provided for manufacturing a splittable medical device that allows preferential tear lines to be formed in and to remain in the distal tip of the medical device even where the distal tip of the medical device is heated to form a tapered distal tip.

We claim:

1. A process for forming a splittable tubular medical device, comprising:

forming a tube having an internal surface, an external surface, a distal portion and a proximal portion;

forming at least one preferential tear line extending longitudinally along the external surface at least along the proximal portion;

placing the tube on a mandrel having a proximal portion and a distal portion and a plurality of longitudinal ribs extending radially outward along the distal portion;

heating at least the distal portion of the tube;

forming a plurality of longitudinally extending grooves along the internal surface of the distal portion of the tube;

engaging the mandrel with a die to form a tapered configuration along the distal portion of the tube; and removing the shaped tube from the die and mandrel.

2. The process of claim 1 wherein at least 8 longitudinally extending grooves are formed along the internal surface of the distal portion of the tube.

3. The process of claim 1 wherein the grooves have a depth of about 0.002 inches.

4. The process of claim 1 wherein the grooves have a first portion with a first depth and a second portion distal to the first portion with a second depth.

5. The process of claim 4 wherein the first depth is about 0.002 inches and the second depth is about 0.0015 inches.

* * * * *